United States Patent [19]

Bolton et al.

[11] Patent Number: 5,039,521

[45] Date of Patent: Aug. 13, 1991

[54] IMMUNE CELL PROLIFERATION INHIBITORS

[75] Inventors: Anthony E. Bolton, Sheffield, England; Alan Drizen, Downsview, Canada

[73] Assignee: Hyal Pharmaceutical Corporation, Mississauga, Canada

[21] Appl. No.: 295,734

[22] Filed: Jan. 11, 1989

[51] Int. Cl.$^5$ .................... A61K 37/02; A61K 39/395
[52] U.S. Cl. ......................................... 424/85.8; 514/2
[58] Field of Search ........................... 514/2; 424/85.8

[56] References Cited

U.S. PATENT DOCUMENTS 4,705,687  11/1987  Lau .
4,748,246   5/1988  Skotnicki et al. .
4,751,305   6/1988  Skotnicki et al. .
4,752,578   6/1988  Moore et al. .
4,766,069   8/1988  Auron et al. .

OTHER PUBLICATIONS

A. G. Pockley et al., "Suppression of In Vitro Lymphocyte Reactivity to Phytohemagglutinin by Placental Protein 14", *Journal of Reproductive Immunology*, vol. 13, 1988, pp. 31-39.

A. E. Bolton et al., "Identification of Placental Protein 14 as an Immunosuppressive Factor in Human Reproduction", *The Lancent*, Mar. 14, 1987, pp. 593-595.

M. Julkunen et al., "Complete Amino Acid Sequence of Human Placental Protein 14: A Progesterone-Regulated Uterine Protein Homologous to Beta-Lactoglobulins", *Proc. Natl. Acad. Sci. U.S.A.*, vol. 85, Dec. 1988, pp. 8845-8849.

Julkunen et al.—Chem. Abst., vol. 104 (1986) pp. 32411s, 163861m.
Bolton et al.—Chem. Abst., vol. 103 (1985) p. 35324f.
Bohn et al.—Chem. Abst., vol. 99 (1983) p. 66147d.
Bell et al.—Chem. Abst., vol. 105 (1986) p. 188,111a.
McGregor—Brit. Med. J., vol. 283, No. 6300 (Oct. 1981) pp. 1143-1144.
Pockley et al., "Placental Protein 14 (PP14) Inhibits the Synthesis of Interleukin-2 and the Release of Soluble Interleukin-2 Receptors from Phytohaemagglutinin-S-timulated Lymphocytes", Clin. Exp. Immunol. (1989) 77, pp. 252-256.
Bolton et al., "The Radioimmunassay of Human Placental Protein 14 (PP14)", Clinica Chimica Acta, 135 (1983) pp. 283-291.
Pockley—Chem. Abst., vol. 111 (1989) p. 113,621g.
An Investigation into the Immunomodulatory Activities of Human Placentral Protein 14 (pp14) *Chem. Abst., vol. 111, (1989) Pockley.*

*Primary Examiner*—Sam Rosen
*Attorney, Agent, or Firm*—Roper & Quigg

[57] ABSTRACT

A method for the treatment of immune system disorders in humans by administration of pp14; derivatives, fragments, or subunits of pp14; or monoclonal antibodies thereto. The method may be used to treat allergic disorders, autoimmune disorders, inflammatory disorders, lymphoproliferation disorders, and neoplastic disorders. Monoclonal antibodies to pp14, and the hybridoma cell lines which produce them. A method for the detection and quantitation of pp14 using monoclonal antibodies thereto, as well as a method for the purification of pp14 using an affinity or immunoprecipitation reaction.

21 Claims, 1 Drawing Sheet

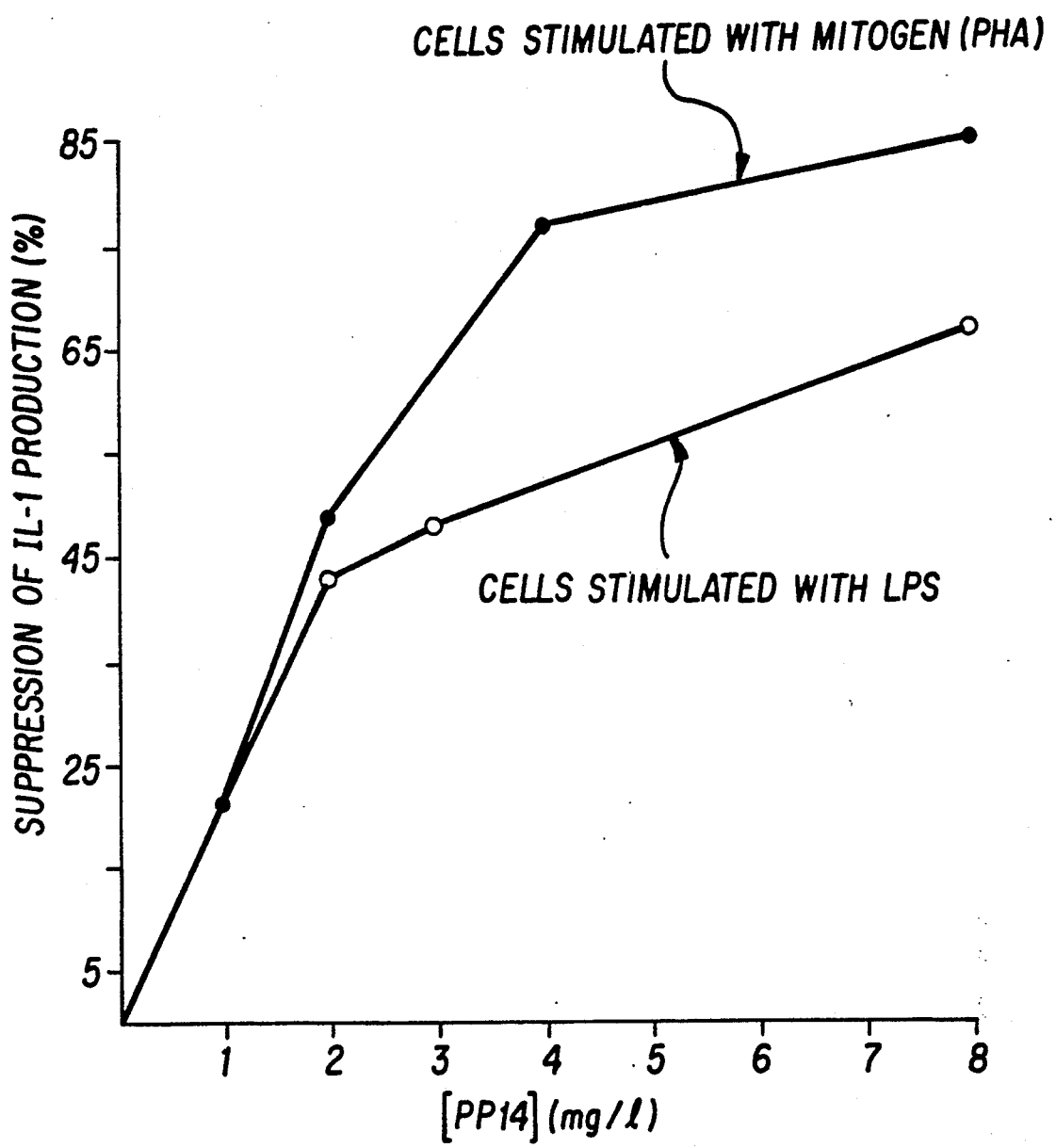

IMMUNE CELL PROLIFERATION INHIBITORS

BACKGROUND OF THE INVENTION

1. Field of the Invention

The present invention relates to inhibitors of immune cell proliferation and function. More particularly the present invention is directed to the use of pp14 as inhibitors of immune cell proliferation and function.

2. Background of the Invention

The human immune system functions to protect the organism from infection and from foreign antigens by cellular and humoral mechanisms. The immune system consists of a complex organization of many types of lymphocytes, and macrophages or other antigen-presenting cells. These agents regulate each other by means of multiple cell-cell interactions and by elaborating soluble factors, including lymphokines and antibodies, that have autocrine, paracrine, and endocrine effects on immune cells. Disorders of the regulation of this system may result in uncontrolled proliferation of immune cells and eventually to malignancy, uncontrolled response to foreign antigens or organisms leading to allergic or inflammatory diseases, aberrant immune responses directed against host cells leading to organ damage and dysfunction, or generalized suppression of the immune response leading to severe and recurrent infections.

Interleukin 1 (IL-1) is a peptide cytokine secreted by a range or variety of cell types including accessory cells of the immune system, the antigen presenting cells, and which has a variety of functions including an involvement in the activation of immune system T-cells. Cells secreting IL-1 include monocytes present in the circulating blood, macrophages found in interstitial fluid, and dendritic cells.

It now appears established that IL-1 is a central mediator of inflammatory reactions and is important in the pathogenesis of chronic inflammatory diseases, of which rheumatoid arthritis (RA) is one example. Evidence for this has been derived from a variety of experimental approaches and may be summarized thus:

1. Prostaglandins and leukotrienes are mediators of inflammatory reactions, hence non-steroidal anti-inflammatory drugs, which inhibit cyclooxygenase and prostaglandin synthesis, are useful therapeutically in such conditions. IL-1 mobilizes free arachidonate, the precursor of prostaglandins and leucotrienes, by activating phospholipases, and also induces cyclooxygenase.

2. IL-1 stimulates binding of T-cells to endothelial cells, thought to be the first step in their influx into joints.

3. Injection of recombinant IL-1 into joints causes an influx of inflammatory cells, followed by a loss of proteoglycan from the cartilage.

Treatment of allergies and autoimmune diseases has been based on modalities which are toxic to immune cells, that inhibit production of antibodies, or inhibit the effects of mediators of the immune response, such as histamine. Over the past several years many soluble lymphokines which regulate the immune system have been characterized. Drugs which allow manipulation of the production of function of such factors would be of use in the treatment of autoimmune diseases and perhaps in the treatment of diseases resulting from uncontrolled proliferation of immune cells.

It is now becoming widely accepted that IL-1 (both IL-1 alpha and IL-1 beta) are important mediators of inflammatory responses. IL-1 appears to directly cause cartilage breakdown in knee joints, and may be central in the pathogenesis of rheumatoid arthritis. An inhibitor may, therefore, be of importance in treatment of this disease. It is of interest that pp14 is a natural product present at elevated levels in the peripheral circulation early in pregnancy, peaking around week 9-10, and there are reports in the literature that there is a marked improvement in some sufferers with rheumatoid arthritis in the first trimester of pregnancy. Similar reports of an improvement of patients with chronic asthma in the first trimester of pregnancy can also be found in the published literature. Chronic asthma is an inflammatory disease, and although IL-1 has not yet been implicated in its etiology, this remains a possibility.

As pp14 appears early in pregnancy, it may be associated with the process of implantation and in maintaining the early conceptus which may be particularly prone to immune rejection by the maternal immune system. It is possible that pp14 could be of utility in the treatment of early miscarriage, which may relate to immune phenomena.

Pregnancy is a normal state in which at least one aspect of the immune response—reaction to foreign antigens—is suppressed in regard to paternal antigens expressed by the fetus. It is rational, therefore, to seek natural inhibitory regulators of the immune response in the tissue or bloodstream of pregnant women. The expression of a variety of proteins is induced to high levels during pregnancy. One of these, pp14, is a major secretory protein of decidual tissue, where it comprises about 10% of the total soluble protein.

SUMMARY OF THE INVENTION

The present invention is directed to a method for treating an immune system disorder in a human by administering to the human a substance selected from the group consisting of pp14, derivatives of pp14, fragments of pp14, and subunits of pp14, in an amount effective to alleviate the disorder. The disorders which may be treated by this method include allergic conditions, autoimmune conditions, and inflammatory conditions.

The substance may be administered to the patient by any appropriate route, including intravenous injection, intramuscular injection, oral administration, topical administration, rectal administration, and inhalation. The substance may be administered in admixture with a pharmaceutically acceptable carrier.

The substance may be obtained from a variety of sources, including mammalian placenta, mammalian blood, amniotic fluid, seminal plasma, cells in tissue culture, decidual cells, decidual organs, endometrial cells, endometrial organs, and recombinant protein sources.

Specific immune system disorders which may be treated according to this method include arthritis, rheumatoid arthritis, asthma, graft-versus-host disease, organ rejection, osteoarthritis, systemic lupus erythematosis, atopic allergy, multiple sclerosis, allergic dermatitis, inflammatory bowel disease, psoriasis, sarcoidosis, and other inflammatory disorders.

In another embodiment, the immune system disorder to be treated according to the present invention may be a lymphoproliferative disorder, such as malignant non-Hodgkins lymphoma, Hodgkin's disease, or malignant histiocystotis.

In a still further embodiment, the discoveries of the present invention may be applied to test inflammatory and autoimmune diseases.

In another still further embodiment, the discoveries of the present invention may be applied to treat autoimmune diseases manifested by infertility.

In a further embodiment, the immune system disorder may be a neoplastic disorder, such as a leukemia.

The present invention is also directed to a method for treating an immune system disorder in a human by administering to the human monoclonal antibodies directed against a substance selected from the group consisting of pp14, derivatives of pp14, fragments of pp14, and subunits of pp14.

The immune system disorder to be treated may be a disorder resulting from the presence in the human of the virus which causes acquired immunodeficiency syndrome.

The monoclonal antibodies may be administered by a method selected from the group consisting of intravenous injection, intramuscular injection, oral administration, topical administration, rectal administration, and inhalation, and may be administered in admixture with a pharmaceutically acceptable carrier.

The present invention extends to a composition of matter comprising monoclonal antibodies directed against a substance selected from the group consisting of pp14, derivatives of pp14, fragments of pp14, and subunits of pp14. The monoclonal antibodies may be specifically directed against pp14.

In yet another embodiment, the present invention includes a hybridoma cell line producing such monoclonal antibodies.

In yet a further embodiment, the present invention is directed to a method for the detection and quantitation of pp14 comprising the steps of:
a) contacting a sample suspected of containing pp14 with the composition in accordance with the present invention; and
b) subjecting the sample to an assay to detect the presence and amount of any antibody-antigen reaction therein.

The assay may be selected from the group consisting of radioimmunoassays, ELISA assays, and immunoblotting assays.

The present invention further includes a method for purifying pp14 from a substance containing pp14, comprising contacting the substance with monoclonal antibodies directed against the pp14, whereby an immunoprecipitation reaction, or antigen: antibody interaction results.

DETAILED DESCRIPTION OF THE INVENTION

Of the range of proteins which have been described as associated with the pregnant state, one has been found to exhibit an immunosuppressive activity in a variety of in vitro tests. Further investigation of the mode of action of this peptide has indicated that it inhibits IL-1 production by peripheral white blood cells (containing both T-lymphocytes and monocytes) after stimulation. The concentration at which this protein is active appears to be the levels at which it is found normally in pregnancy. The time course of this inhibition of IL-1 production closely relates to the immunosuppressive activity of the molecule, indicating that its primary effect is on monocytes rather than other immune system cells.

The pregnancy-associated protein, i.e. pp14, is shown to inhibit IL-1 production by stimulated macrophages and to inhibit monocytes lymphokine secretion, IL-2 receptor expression, and proliferation of mitogen or allogeneically stimulated lymphocytes.

Treatment of autoimmune, allergic, inflammatory, or lymphoproliferative disorders may thus be effected by administration of pp14 to patients.

Specific immune system disorders which may be treated according to this method include arthritis, rheumatoid arthritis, asthma, graft-versus-host disease, organ rejection, osteoarthritis, systemic lupus erythematosis, atopic allergy, multiple sclerosis, allergic dermatitis, inflammatory bowel disease, psoriasis, sarcoidosis, and other inflammatory disorders.

In another embodiment, the immune system disorder to be lymphoproliferative disorder, such as malignant non-Hodgkin's lymphoma, Hodgkin's disease, or malignant histiocystosis.

In another still further embodiment, the discoveries of the present invention may be applied to treat autoimmune diseases manifested by infertility.

In a further embodiment, the immune system disorder may be a neoplastic disorder, such as leukemia.

The pp14 substance may be obtained from a variety of sources, including mammalian placenta, mammalian blood, amniotic fluid, seminal plasma, cells in tissue culture, decidual cells, decidual organs, endometrial cells, endometrial organs, and recombinant protein sources.

The pp14 substance is obtained from a source selected from the group consisting of mammalian placenta, mammalian blood, amnionic fluid, seminal plasma, cells in tissue culture, decidual cells, decidual organs, endometrial cells, endometrial organs, and sources containing eukaryotic cells and prokaryotic cells engineered to express pp14, fragments of pp14 and subunits of pp14.

The present invention is also directed to a method for treating an immune system disorder in a human by administering to the human monoclonal antibodies directed against a substance selected from the group consisting of pp14, derivatives of pp14, fragments of pp14, and subunits of pp14.

A monoclonal antibody directed against pp14 has been isolated. This antibody is used to detect and to quantitate in vivo levels of pp14. Administration of the antibody to mammals may neutralize physiologic and pathophysiologic actions of pp14.

The immune system disorder to be treated may be a disorder resulting from the presence in the human of the virus which causes acquired immunodeficiency syndrome.

The monoclonal antibodies may be administered by a method selected from the group consisting of intravenous injection, intramuscular injection, oral administration, topical administration, rectal administration, and inhalation, and may be administered in admixture with a pharmaceutically acceptable carrier.

The present invention extends to a composition of matter comprising monoclonal antibodies directed against a substance selected from the group consisting of pp14, derivatives of pp14, fragments of pp14, and subunits of pp14. The monoclonal antibodies may be specifically directed against pp14.

In this application, the immunoregulatory properties of pp14 in suppressing lymphokine secretion and lymphoproliferation is described.

It is an object of the present invention to provide, with pp14, a new modality for the treatment of autoimmune and lymphoproliferative disorders.

Another embodiment of the invention is the isolation of a monoclonal antibody to pp14 which can be utilized for its detection and quantitation. Such an antibody can also be used to facilitate efficient purification of the factor. Inhibition of pp14 activity by binding it to an antibody can be used in vitro to study its cellular and biochemical effects and in vivo in animals to study its effects on mammalian biology. Disorders in which the immune response is abnormally suppressed or attenuated may potentially be treated by inhibiting pp14 activity with such an antibody.

In yet another embodiment, the present invention includes a hybridoma cell line producing such monoclonal antibodies.

In yet a further embodiment, the present invention is directed to a method for the detection and quantification of pp14 comprising the steps of:
a) contacting a sample suspected of containing pp14 with the composition in accordance with the present invention; and
b) subjecting the sample to an assay to detect the presence and amount of an antibody:antigen reaction therein.

The assay may be selected from the group consisting of radioimmunoassays, ELISA assays, and immunoblotting assays.

The present invention further includes a method for purifying pp14 from a substance containing pp14, comprising contacting the substance with monoclonal antibodies directed against the pp14, whereby an immunoprecipitation reaction, or antigen:antibody interaction results.

The present invention is directed to the definition of the immunoregulatory properties of pp14 and methods of for using these properties in the treatment of autoimmune, inflammatory, allergic and neoplastic disorders of humans and other mammals.

pp14 is shown to inhibit mitogenic stimulation of proliferation and secretion of interferon and IL-2 by lymphocytes. A similar inhibition of allogeneic stimulation of lymphocytes is also measured. These effects are accompanied by a reduction in the affinity of high affinity lymphocyte IL-2 receptors and an inhibition of the expression of functional IL-2 receptors.

pp14 suitable for purposes of the present invention is material found to be present in extracts of human decidual tissue which binds to the monoclonal antibody used in accordance with the present invention. The activities observed from in vitro test systems correlate with the pp14 content of tissue extracts, and other preparations as measured in a radioimmunoassay for pp14 which utilizes a polyclonal antibody. This radioimmunoassay is described in Anthony E. BOLTON et al., "The Radio Immuno Assay of Human Placental Protein 14 (pp14), Clinica Chimica Acta, 135 (1983) 283-291 Elsevie Bar. The pp14 suitable for purposes of the present invention has been observed to be functional in the inhibition of the proliferation of mitogen and allogeneically stimulated peripheral blood mononuclear cells; the inhibition of the production and/or release of IL-1 by stimulated peripheral blood mononuclear cells; and the reduction in the affinity abiding of IL-2 to stimulated peripheral blood mononuclear cells.

Activation of the immune regulatory and proliferative capacity of lymphocytes is a complex process mediated by a number of lymphokines and requiring the cooperation of accessory cells. These cells secrete the lymphokine IL-1 in response to antigenic stimulation. This factor is required for the expression of the IL-2 receptor by lymphocytes which then respond mitogenically to IL-2.

pp14 inhibits the elaboration of IL-1 by activated or stimulated peripheral blood monocyte; this may account for many of the modulating activities of pp14. Similar suppressive effects are induced by crude decidual extracts; this activity is abolished by antibody to pp14. Thus, pp14 has been discovered to have immunosuppressive activity related to its ability to decrease expression or secretion of IL-1 and possibly independent effects on lymphocyte secretion and proliferation.

Many human diseases result from an abnormal, unregulated proliferation of lymphocytes, or from an uncontrolled immune response direct against the patient's own cells or tissues. Some of these defects may result from elevated, unregulated secretion of lymphokines. An example is rheumatoid arthritis, in which IL-1 has been shown to activate synovial prostaglandin and leukotriene production, enhance T-cell binding to endothelia, and to reproduce several aspects of the condition in animal models. Similar evidence exists for other chronic inflammatory diseases. pp14, an inhibitor of IL-1 production, is a potential treatment modality for such diseases, including syndromes such as asthma, which is characterized by excessive secretion of leukotrienes in the bronchial tree, and allergic dermatitis and inflammatory bowel diseases, which are characterized by chronic overproduction of mediators of inflammation.

Other autoimmune diseases, such as systemic lupus erythematosis, Sjogren's syndrome, and scleroderma are characterized by abnormal ratios of a variety of different types of T- and B- lymphocytes which may result from defective regulation of their proliferation. More extreme losses of regulation of growth may be accompanied by further genetic changes in the cell and result in overgrowth of a malignant clone of cells leading to a malignancy in the patient. Such malignant cells often still require autocrine or paracrine stimulation by a lymphokine growth factor in order to drive their proliferation.

Inhibition of expression of these factors or of their receptors by pp14 could be an effective mode for treatment of these patients.

The precise physiologic role and regulation of pp14 and whether it ever functions or is expressed abnormally in human disease is unknown.

pp14 is a glycoprotein comprising about 17.5% carbohydrate content. The details of this carbohydrate content are not presently known; however, pp14 binds strongly to the lectin concanavalin-A, which is known to have an affinity for terminal alpha-D-mannosyl and alpha-D-glucosyl residues, as well as to wheat germ agglutinin, which has an affinity for N-acetyl-beta-D-glucosaminyl residues. The presence of the latter is further evidenced by the reduction of the interaction of pp14 with specific antibodies caused by treatment of pp14 with the enzyme beta-N-acetyl glucosaminidase, which removes these residues.

While the complete amino acid sequence has not yet been established, it appears that the 24 N-terminal amino acids are:

Met-Asp-Ileu-Pro-GluNH2-Thr-Lys-GluNH2Asp-
Leu-Glu-Leu-Pro-Lys-Leu-Ala-Gly-Thr-Glu-His-
Glu-Met-Ala-Met- The N-terminal amino acid sequence shows substantial sequence homology with certain animal B-lactoglobulins, but the biological activities of these proteins are not well understood. Furthermore, there is some sequence homology with human serum retinol binding protein.

The activation of lymphocytes, resulting in cell proliferation is a complex response mediated by a number of peptide messengers, the cytokines. At a simplified level, T-lymphocytes are activated by a sequential process. Firstly, there is a requirement for the cytokine Interleukin-1 (IL-1) secreted by accessory cells (e.g. cells of the monocyte/macrophage lineage). In the presence of IL-1 the cytokine Interleukin-2 (IL-2) increases the expression of its own receptors, making the cell more responsive to IL-2 - a positive feedback cycle. IL-2 also stimulates T-cell division (lymphoproliferation). Thus, the proliferation of T-cells requires the presence of both IL-1 and IL-2.

One approach to investigating the mode of action of lymphoproliferation with an inhibitor such as pp14 is to add an excess of cytokine along with the inhibitor and see if the suppression is reversed. One source of a crude mixture of cytokines is the supernatant taken from cultured activated lymphocytes. Such supernatants were demonstrated to reverse the suppressive action of pp14, indicating a mode of action relating to the secretion/activity of cytokine. The addition of recombinant IL-1 at a single dose significantly reduced the suppressive action of pp14 on lymphoproliferation, as shown in the following Table:

TABLE 1

This table shows the effect of the addition of 5 U/ml of recombinant IL-1 on the suppression of tritiated thymidine uptake by stimulated lymphocytes.

| Decidual sample no. | pp14 (ng/ml) | % suppression of 3H-Tdr +IL-1 | % suppression of 3H-Tdr −IL-1 |
| --- | --- | --- | --- |
| DE A | 5.0 | 25 | 30 |
| DE B | 4.8 | 12 | 62 |
| DE C | 4.0 | 25 | 46 |
| DE D | 8.0 | 33 | 48 |
| DE E | 2.0 | 30 | 41 |

Mean (+/−S.D.)

These data indicate that pp14 may be operating via an IL-1-mediated mechanism.

To investigate this possibility further, peripheral blood mononuclear cells (a mixture primarily of T-cells and monocytes) were activated using the mitogen PHA in the presence and absence of inhibitory amounts of pp14. The amount of IL-1 released into the supernatants of the cultured cells was measured after different times of culture. The results from the two experiments carried out are shown in the attached figure, and the data are given in the Table below. It can be seen that pp14 significantly inhibited the release of IL-1 into the supernatant by activated cells. These data on IL-1 strongly suggest that pp14 is acting at the IL-1 level of T-cell activation by inhibiting its synthesis/release.

TABLE 2

This Table shows the effect of pp14 in decidual extracts on the release into cell culture supernatants of IL-1 by stimulated peripheral blood lymphocytes.

Experiment 1.

| | TIME (hours) | | | |
| --- | --- | --- | --- | --- |
| | 22.5 | 41 | 65 | 89 |
| Unstimulated | 0.2 | 0.2 | 0.1 | 0.1 |
| Immunoabsorbed extract | 1.583 | 1.266 | 1.232 | 1.196 |
| Unabsorbed extract | 0.406 | 0.216 | 0.212 | 0.2 |
| % Suppression | 75% | 83% | 91% | 83% |

Experiment 2.

| | TIME (hours) | | | |
| --- | --- | --- | --- | --- |
| | 18 | 42 | 66 | 80 |
| Unstimulated | 0.6 | 0.2 | 0.4 | 0.3 |
| Immunoabsorbed extract | 1.789 | 2.554 | 2.709 | 2.807 |
| Unabsorbed extract | 0.7 | 1.162 | 1.630 | 1.967 |
| % Suppression | 61% | 55% | 40% | 30% |

NOTES
Unstimulated—spontaneous release of IL-1 from unstimulated lymphocytes.
Immunoabsorbed extract—IL-1 release from stimulated cells in the presence of a crude decidual extract from which pp14 had been specifically removed by monoclonal antibody immunoabsorption.
Unabsorbed extract IL-1 release from stimulated lymphocytes in the presence of a crude decidual extract containing 8.0 ug/ml pp14.
% suppression—the suppression of IL-1 released into the cell culture supernatants by pp14 in decidual extracts, expressed as a % of the release of IL-1 in the presence of decidual extracts from which pp14 had been removed.

Individual results for each experiment are means of triplicate determinations.

A monoclonal antibody which specifically binds to pp14 has been isolated and characterized. This monoclonal antibody is designated MAb 14/1/1, and was derived from hybridomal cell lines produced by fusion, using a polyethylene glycol method of spleen cells from mice immunized with crude extracts of decidual with the myeloma cell line P3/NS1/1-Ag4-1, which is a standard myeloma cell line. Clones secreting anti-pp14 were selected using the radiolabelled pp14 used for the radioimmunoassay (BOLTEN et al., 1983, supra). Positive cultures were cloned three times by limiting dilution and those yielding the highest titers used to induce tumors in Balb/C mice. IgG was isolated from ascitic fluid from ion exchange chromatography or affinity chromatography on protein-A.

The specificity of the antibody was examined in two ways. First, the two-site immunoradiometric assay was set up using a polyclonal extracting antibody and the monoclonal as labelled antibody. Polyclonal antibody, raised against crude decidual tissue extract was covalently linked to Sepharose-4B by standard procedures. This was incubated in excess in the presence of standard pp14 or the potentially cross-reacting protein for two hours at room temperature. Subsequently, radioiodinated monoclonal antibody was added, incubated a further two hours, and the solid-coupled antibody washed and counted for radioactivity. This represents a conventional 2-site immunoradiometric assay. The cross-reaction of various decidual/placenta proteins was investigated in this system. The following gave less than 0.1% cross reaction: hPL, SP1, pp5, pp12, pregnancy-associated plasma protein-A (PAPP-A), placental alkaline phosphates, placental malic dehydrogenase, placental sphyngomyelinase placental arylamidase, placental chlorine acetyltransferase, with only pp14 having any observed activity in this assay. The other method involved investigating the binding to the monoclonal antibody of radioactively-labelled pure proteins. No significant binding of prolactin, hCG, or PAPP-A was detected. This antibody could be used in the assay, for example by a two-site immunoradiometric procedure, and purification of pp14. As previously mentioned, the details of the radioimmunoassay for pp14 are disclosed in the BOLTEN et al. article, identified above.

EXAMPLES

Example 1

Evidence that pp14 inhibits IL-1 release

Method 1—the mitogenic response of human lymphocytes

Human peripheral blood lymphocytes proliferate in response to stimulation by the mitogen phytohaemagglutinin (PHA), the proliferation being measured by the incorporation of tritiated thymidine into the DNA of the dividing cells. This is a standard test of lymphocyte responsiveness. pp14 inhibits lymphocyte proliferation in response to PHA stimulation. The addition of recombinant ILI partially reverses the inhibition caused by pp14.

The test system used in this method is to investigate the effect of recombinant IL-1 on the mitogen-induced stimulation of pp14-inhibited peripheral blood lymphocytes. The use of pp14-inhibited cells in experiments such as this is unique methodology.

The pp14 inhibition of cells in this work is carried out as follows. Cells are treated with crude extracts of human decidual in which the pp14 concentration is measured by radioimmunoassay. As a control for each treated cell preparation, a portion of the cells are treated with the same extract that has been immunoabsorbed using a monoclonal antibody to pp14, MAb/pp14/1/1, to remove the pp14 in a highly specific manner. The difference between the activity of the cells treated with these two preparations represents the effect of pp14. Thus, the effects measured are those of pp14 which specifically binds to this monoclonal antibody. Peripheral blood mononuclear cells are isolated from whole blood obtained from healthy donors by a standard density gradient centrifugation method. After washing in a physiological medium, the cells are resuspended at an appropriate concentration of viable cells and incubated in the presence of the pp14 preparation and the mitogen at a stimulatory concentration.

The effects of IL-1, or other test compound, are assessed by inclusion at appropriate concentrations in this incubation, including also the necessary controls. The cells are incubated for 72 hours at 37° C. in an atmosphere of 5% carbon dioxide and 100% humidity under sterile conditions. Six hours prior to termination of the cultures, the cells are pulsed with 1 uCi of tritiated thymidine, and on termination the cells are harvested automatically onto glass fiber filters.

The degree of lymphoproliferation is assessed by measuring the incorporation of tritiated thymidine into the harvested cells by liquid scintillation counting.

Inhibition of tritiated thymidine uptake by pp14, and the effect of IL-1:

| % inhibition of tritiated thymidine uptake | |
|---|---|
| Without IL-1 | With 5 U/ml IL-1 |
| 45.4 ± 11.6 | 25.0 ± 8.0 |

These are mean results from 15 different experiments, each performed in triplicate, using 5 different decidual extracts as the source of pp14 and cells from 2 separate donors. The results are significantly different (p<0.0001), indicating a significant reversal of the inhibitory effect of pp14 on lymphoproliferation by IL-1.

Example 2

The effect of pp14 on the production of IL-1 by stimulated peripheral blood mononuclear cells Background Peripheral blood mononuclear cells, as isolated by density gradient centrifugation, contain not only lymphocytes (the majority of the cells present) but also monocyte/macrophages, which are necessary accessory cells in the lymphoproliferative reaction described above. It is this latter cell type which synthesizes and secretes IL-1. These cells can be activated to secrete their specific products which include IL-1 by both mitogens (eg PHA) and lipopolysaccharide (LPS).

The test system used in this method is to investigate the production of macrophage/monocyte products released from stimulated pp14-inhibited peripheral blood mononuclear cell preparations, measuring the products by commercially available immunoassay systems. The use of pp14-inhibition of cells is carried out as in Method 1 above, which again is unique methodology.

Peripheral blood mononuclear cells are prepared as under Method 1. Appropriate numbers of cells are incubated in the presence of the pp14 preparation and the stimulator for various times under the conditions described above. At the termination of the culture period the cells are harvested and the supernatants assayed for IL-1 and Tumour Necrosis Factor (TNF), both known to be products of macrophage/monocyte cells.

Typical results are summarized below.

Inhibition of IL-1 release by stimulated peripheral mononuclear cells by pp14:

| % inhibition of IL-1 release | |
|---|---|
| PHA stimulated cells | LPS stimulated cells |
| 82.5 | 67.0 |

These are mean results from 3 experiments.

This inhibition of IL-1 release from stimulated (using either PHA or LPS) mononuclear cells by pp14 is dose dependant, as shown in the Figure, wherein
• cells stimulated with mitogen (PHA)
o represent cells stimulated with LPS

Example 3

Comparison of IL-1 and TNF production by pp14-inhibited stimulated peripheral blood mononuclear cells:

Cells stimulated with mitogen:

|  | IL-1 produced % inhibition | TNF produced % inhibition |
|---|---|---|
| stimulated control | 2.60 ng/ml | 1043 pg/ml |
| +pp14 (4 ug/l) | 0.46 ng/ml | 1474 pg/ml |

From the foregoing description, one skilled in the art can easily ascertain the essential characteristics of the invention and, without departing from the spirit and scope thereof, can make various changes and modifications of the invention and adapted to various usages and conditions.

What is claimed is:

1. A method for treating an immune system disorder in a human by administering to said human an effective therapeutic amount of pp14, to alleviate said immune system disorder.

2. The method as defined by claim 1, wherein said immune system disorder is selected from the group consisting of allergic conditions, autoimmune conditions, and inflammatory conditions.

3. The method as defined by claim 2, wherein said substance is administered by a method selected from the group consisting of intravenous injection, intramuscular injection, oral administration, topical administration, rectal administration, and inhalation.

4. The method as defined by claim 2, wherein said substance is obtained from a source selected from the group consisting of mammalian placenta, mammalian blood, amniotic fluid, seminal plasma, cells in tissue culture, decidual cells, decidual organs, endometrial cells, endometrial organs, and sources containing eukaryotic cells and prokaryotic cells engineered to express pp14.

5. The method as defined by claim 2, wherein said immune system disorder is selected from the group consisting of arthritis, rheumatoid arthritis, asthma, graft-versus-host disease, organ rejection, systemic lupus erythematosis, atopic allergy, inflammatory bowel disease, multiple sclerosis, and allergic dermatitis.

6. The method as defined by claim 5, wherein said autoimmune conditions are manifested by infertility.

7. The method as defined by claim 5, wherein said substance is administered in admixture with a pharmaceutically acceptable carrier.

8. The method as defined by claim 1, wherein said immune system disorder comprises a lymphoproliferative disorder.

9. The method as defined by claim 8, wherein said substance is administered by a method selected from the group consisting of intravenous injection, intramuscular injection, oral administration, topical administration, rectal administration, and inhalation.

10. The method as defined by claim 8, wherein said substance is obtained from a source selected from the group consisting of mammalian placenta, mammalian blood, amniotic fluid, seminal plasma, cells in tissue culture, decidual cells, decidual organs, endometrial cells, and endometrial organs and recombinant protein sources.

11. The method as defined by claim 10, wherein said lymphoproliferative disorder is selected from the group consisting of malignant non-Hodgkins lymphoma, Hodgkin's disease, and malignant histiocytotis.

12. The method as defined by claim 1, wherein said immune system disorder is a neoplastic disorder.

13. The method as defined by claim 12, wherein said neoplastic disorder is a leukemia.

14. A method for treating an immune system disorder in a human by administering to said human an effective therapeutic amount of monoclonal antibodies directed against pp14.

15. The method as defined by claim 14, wherein said immune system disorder is a disorder resulting from the presence in said human of the virus which causes acquired immunodeficiency syndrome.

16. The method as defined by claim 14, wherein said monoclonal antibodies are administered by a method selected from the group consisting of intravenous injection, intramuscular injection, oral administration, topical administration, rectal administration, and inhalation.

17. The method as defined by claim 14, wherein said monoclonal antibodies are administered in admixture with a pharmaceutically acceptable carrier.

18. A method for inhibiting Interleukin-1 production in a human, which comprises: administering to said human an effective therapeutic amount of pp14, in an amount effective to inhibit said Interleukin-1 production.

19. The method as defined in claim 18 wherein said substance is administered by means selected from the group consisting of intravenous injection, intramuscular injection, oral administration, topical administration, rectal administration, and inhalation.

20. The method as defined by claim 18, wherein said substance is obtained from a source selected from the group consisting of mammalian placenta, mammalian blood, amniotic fluid, seminal plasma, cells in tissue culture, decidual cells, decidual organs, endometrial cells, endometrial organs, and sources containing eukaryotic cells and prokaryotic cells engineered to express pp14.

21. The method as defined by claim 18, wherein said substance is administered in admixture with a pharmaceutically acceptable carrier.

* * * * *